(12) United States Patent
Wang et al.

(10) Patent No.: US 8,542,324 B2
(45) Date of Patent: Sep. 24, 2013

(54) EFFICIENT IMAGE AND VIDEO RECOLORING FOR COLORBLINDNESS

(75) Inventors: Meng Wang, Beijing (CN); Linjun Yang, Beijing (CN); Xian-Sheng Hua, Beijing (CN); Bo Liu, Hong Kong (CN)

(73) Assignee: Microsoft Corporation, Redmond, WA (US)

( * ) Notice: Subject to any disclaimer, the term of this patent is extended or adjusted under 35 U.S.C. 154(b) by 578 days.

(21) Appl. No.: 12/790,176

(22) Filed: May 28, 2010

(65) Prior Publication Data

US 2011/0293177 A1 Dec. 1, 2011

(51) Int. Cl.
*H04N 9/12* (2006.01)
(52) U.S. Cl.
USPC .......................................... 348/742; 382/162
(58) Field of Classification Search
USPC ........................................................ 348/742
See application file for complete search history.

(56) References Cited

U.S. PATENT DOCUMENTS

| | | | |
|---|---|---|---|
| 5,909,220 A * | 6/1999 | Sandow | 345/589 |
| 6,396,948 B1 * | 5/2002 | Lynch et al. | 382/166 |
| 6,560,361 B1 * | 5/2003 | Collins | 382/203 |
| 6,628,828 B1 * | 9/2003 | Stokes et al. | 382/167 |
| 6,674,436 B1 * | 1/2004 | Dresevic et al. | 345/472 |
| 7,145,571 B2 | 12/2006 | Jones et al. | |
| 7,333,117 B2 | 2/2008 | Kim | |
| 7,605,930 B2 | 10/2009 | Suzuki et al. | |
| 7,873,213 B2 * | 1/2011 | Speigle et al. | 382/167 |
| 2003/0095705 A1 * | 5/2003 | Weast | 382/167 |
| 2004/0212815 A1 * | 10/2004 | Heeman et al. | 358/1.9 |
| 2006/0033880 A1 | 2/2006 | Korneluk | |
| 2007/0091113 A1 * | 4/2007 | Jones et al. | 345/592 |
| 2007/0182755 A1 * | 8/2007 | Jones et al. | 345/592 |
| 2008/0089581 A1 * | 4/2008 | Pitie et al. | 382/162 |
| 2009/0128871 A1 | 5/2009 | Patton et al. | |
| 2009/0135266 A1 * | 5/2009 | Raaymakers et al. | 348/222.1 |

OTHER PUBLICATIONS

Huang, Wu, Chen, "Enhancing Color Representation for the Color Vision Impaired", retrieved on Apr. 16, 2010 at <<http://www.ski.org/Rehab/Coughlan_lab/General/CVAVI08pubs/EnhancingColor.pdf>>, Proceedings of European Conference on Computer Vision (ECCV): Workshop on Computer Vision Applications for the Visually Impaired, Oct. 18, 2008, pp. 1-12.

Huang, Chen, Jen, Wang, "Image Recolorization for the Colorblind", retrieved on Apr. 16, 2010 at <<http://ieeexplore.ieee.org/stamp/stamp.jsp?tp=&arnumber=4959795>>, IEEE Computer Society, Proceedings of Conference on Acoustics, Speech and Signal Processing (ICASSP), 2009, pp. 1161-1164.

Huang, Tseng, Wu, Wang, "Information Preserving Color Transformation for Protanopia and Deuteranopia", retrieved on Apr. 16, 2010 at <<http://www.sciweavers.org/publications/information-preserving-color-transformation-protanopia-and-deuteranopia>>, IEEE Signal Processing Letters, vol. 14, No. 10, Oct. 2007, pp. 711-714.

(Continued)

*Primary Examiner* — Jingge Wu
(74) *Attorney, Agent, or Firm* — Lee & Hayes, PLLC

(57) ABSTRACT

Colors of images and videos are modified to make differences in the colors more perceptible to colorblind users. An exemplary recoloring process utilizes a color space transformation, a local color rotation and a global color rotation to transform colors of visual objects from colors which may not be distinguishable by the colorblind user to colors which may be distinguishable by the colorblind user.

16 Claims, 8 Drawing Sheets

(56) References Cited

OTHER PUBLICATIONS

Iaccarino, Malandrino, Del Percio, Scarano, "Efficient Edge-Services for Colorblind Users", retrieved on Apr. 16, 2010 at <<http://www2006.org/programme/files/pdf/p147.pdf>>, ACM, Proceedings of Conference on World Wide Web (WWW), May 22, 2006, pp. 919-920.

Jefferson, Harvey, "Accommodating Color Blind Computer Users", retrieved on Apr. 16, 2010 at <<http://portal.acm.org/citation.cfm?id=1168996>>, ACM, Proceedings of Conference on Computers and Accessibility (ASSETS), Oct. 22, 2006, pp. 40-47.

Jefferson, Harvey, "An Interface to Support Color Blind Computer Users", retrieved on Apr. 16, 2010 at <<http://portal.acm.org/citation.cfm?id=1240855>>, ACM, Proceedings of Conference on Human Factors in Computing Systems (CHI), Apr. 2007, pp. 1535-1538.

Kuhn, Oliveira, Fernandes, "An Efficient Naturalness-Preserving Image-Recoloring Method for Dichromats", retrieved on Apr. 16, 2010 at <<http://ieeexplore.ieee.org/stamp/stamp.jsp?tp=&arnumber=4658199>>, IEEE Transactions on Visualization and Computer Graphics, vol. 14, No. 6, Nov. 2008, pp. 1747-1754.

Lienhart, "Comparison of Automatic Shot Boundary Detection Algorithms", retrieved on Apr. 16, 2010 at <<http://www.lienhart.de/spie99.pdf>>, Proceedings of Conference on Storage and Retrieval for Image and Video Databases (SPIE), vol. 3656, Jan. 1999, pp. 290-301.

Rasche, Geist, Westall, "Re-coloring Images for Gamuts of Lower Dimension", retrieved on Apr. 16, 2010 at <<http://citeseerx.ist.psu.edu/viewdoc/download?doi=10.1.1.143.3602&rep=rep1&type=pdf>>, The Eurographics Association and Blackwell Publishing, Computer Graphics Forum, vol. 24, No. 3, Sep. 2005, pp. 423-432.

"Vischeck", retrieved on Apr. 16, 2010 at <<http://www.vischeck.com>>, Vischeck, 2008, pp. 1.

Wakita, Shimamura, "SmartColor: Disambiguation Framework for the Colorblind", retrieved on Apr. 16, 2010 at <<http://portal.acm.org/ft_gateway.cfm?id=1090815&type=pdf&coll=GUIDE&dl=GUIDE&CFID=86394227&CFTOKEN=56991289>>, ACM, Proceedings of Conference on Computers and Accessibility (ASSETS), Oct. 2005, pp. 158-165.

Yang, Ro, "Visual Content Adaptation for Color Vision Deficiency", retrieved on Apr. 16, 2010 at <<http://ieeexplore.ieee.org/iel5/8824/27937/01246996.pdf?arnumber=1246996>>, IEEE International Conference on Image Processing (ICIP), vol. 1, Sep. 2003, pp. I-453 to I-456.

Zhang, Hua, Lu, "AVE—Automated Home Video Editing", retrieved on Apr. 16, 2010 at <<http://research.microsoft.com/en-us/um/people/llu/publications/acmmm03_ave.pdf>>, ACM, Conference on Multimedia (MM), 2003, pp. 490-497.

* cited by examiner

EFFICIENT IMAGE AND VIDEO RECOLORING FOR COLORBLINDNESS

BACKGROUND

Colorblindness, formally referred to as color vision deficiency, affects about 8% of men and 0.8% of women globally. Colorblindness causes those affected to have a difficult time discriminating certain color combinations and color differences. Colors are perceived by viewers through the absorption of photons followed by a signal sent to the brain indicating the color being viewed. Generally, colorblind viewers are deficient in the necessary physical components enabling them to distinguish and detect particular colors. As a result of the loss of color information, many visual objects, such as images and videos, which have high color quality in the eyes of a non-affected viewer, cannot typically be fully appreciated by those with colorblindness.

Several research works have been dedicated to helping such users better perceive visual objects with color combinations and color differences that are difficult for those with colorblindness to detect. One approach is to recolor the objects, that is, adopt a mapping function to change the colors of the original images, such that the colors that are difficult for the colorblind users to distinguish are mapped to other colors that can be distinguished. However, many recoloring approaches have two major flaws. First, they have huge computational costs. Many methods adopt an optimization process to determine the color mapping function. This introduces large computational costs, and thus they can hardly be applied in real-world applications, especially in real-time video recoloring which typically requires each frame to be processed in less than 1/24 of a second. Second, many recoloring approaches have a color inconsistency problem. For example, the color mapping function may depend on the distribution of colors, i.e., the mapping function will be different for different images. This is not a problem for still images, but it will degrade a user's experience in video recoloring. For example, in two nearby frames, the colors of a particular person's face may be mapped to different colors, and this may confuse the user.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

In view of the above, this disclosure describes a recoloring process for modifying the colors of an image and a video.

In an exemplary implementation, an image is transformed from an original color space to a more desirable color space. For example the image may be transformed from a red, green, blue (RGB) color space to a more usable color space such as a CIE L*a*b* (CIELAB) color space. The image may then undergo a series of rotations, including a local color rotation and a global color rotation. After undergoing the series of rotations, the image may be presented to, and better perceived by, a colorblind user.

A similar recoloring process is also used to recolor images within a video. For example, images determined to be within a single video shot may be transformed based upon calculated parameters. Images within adjacent shots may also be transformed based upon the same calculated recoloring parameters. For example, if the adjacent shots are determined to be within a set proximity threshold and therefore are determined to be associated to one another, then the calculated recoloring parameters may be applied to images within two adjacent shots.

BRIEF DESCRIPTION OF THE DRAWINGS

The detailed description is described with reference to the accompanying figures. In the figures, the left-most digit of a reference number identifies the figure in which the reference number first appears. The use of the same reference numbers in different figures indicates similar or identical items.

DETAILED DESCRIPTION

A recoloring process for modifying the colors of images and videos to make differences in colors within the images and videos more perceptible by colorblind users is described. More specifically, an exemplary recoloring process utilizes a local color rotation and a global color rotation to transform colors of visual objects such that a colorblind user is able to distinguish colors they might otherwise not be able to distinguish.

Figure 1:
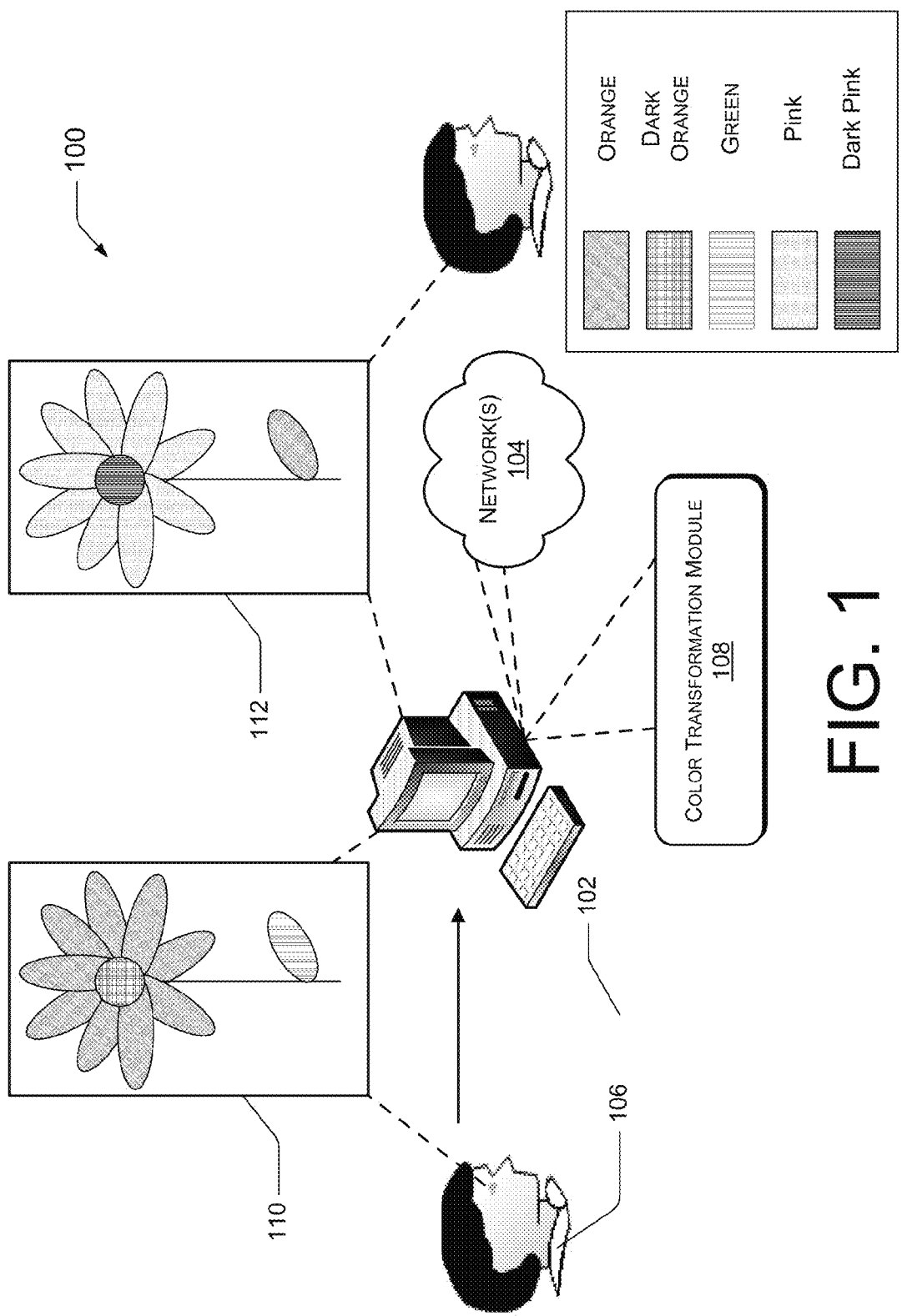
FIG. 1 is a schematic of an illustrative environment of a recoloring framework.

FIG. 1 is a block diagram of an exemplary environment 100, which is used for recoloring an image or video on a computing device. The environment 100 includes an exemplary computing device 102, which may take a variety of forms including, but not limited to, a portable handheld computing device (e.g., a personal digital assistant, a smart phone, a cellular phone), a laptop computer, a desktop computer, a media player, a digital camcorder, an audio recorder, a camera, or any other similar device. The computing device 102 may connect to one or more networks(s) 104 and is often associated with a user 106.

The network(s) 104 represent any type of communications network(s), including, but not limited to, wire-based networks (e.g., cable), wireless networks (e.g., cellular, satellite), cellular telecommunications network(s), and IP-based telecommunications network(s) (e.g., Voice over Internet Protocol networks). The network(s) 104 may also include a traditional landline or a public switched telephone network (PSTN), or combinations of the foregoing (e.g., Unlicensed Mobile Access or UMA networks, circuit-switched telephone networks or IP-based packet-switch networks).

The computing device 102 accesses a color transformation module 108 that transforms colors of a visual object 110 resulting in a transformed visual object 112. The visual object 110 represents the original image and color(s) displayed to the user 106. The transformed object 112 represents a re-colored image using the color transformation module 108, and displays an image which may be better perceived by a colorblind user. While the visual object 110 and the transformed visual object 112 are represented as images in FIG. 1, the visual object 110 and the transformed visual object 112 may also include, without limitation, a real-time video object, a non-real time video object, or a combination of the two. Sources of substantially real-time content generally includes those sources for which content is changing over time, such as, for example, live television or radio, webcasts, or other transient content. Non-real time content sources generally include fixed media such as, for example, pre-recorded video, audio, text, multimedia, games, or other fixed media readily accessible to the user 106.

Figure 2:
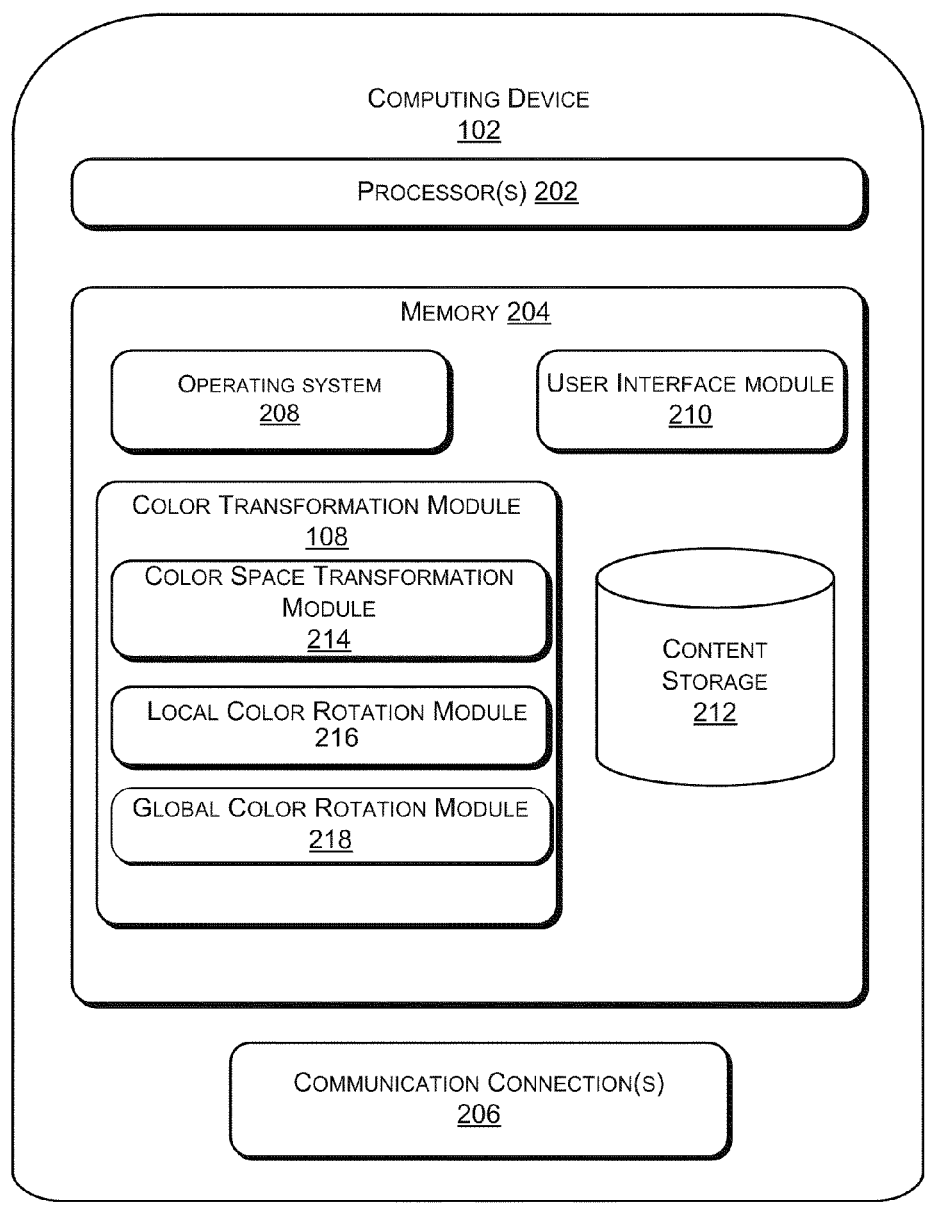
FIG. 2 is a block diagram of an exemplary computing device within the recoloring framework of FIG. 1.

FIG. 2 illustrates an exemplary computing device 102. The computing device 102 includes, without limitation, processor(s) 202, a memory 204, and one or more communication connection 206. An operating system 208, a user interface (UI) module 210, a color transformation module 108, and a content storage 212 are maintained in memory 204 and executed on the processor 202. When executed on the processor 202, the operating system 208 and the UI module 210 collectively facilitate presentation of a user interface on a display of the computing device 102.

Color transformation module 108 includes, without limitation, a color space transformation module 214, a local color rotation module 216, and a global color rotation module 218. Color transformation module 108 may be implemented as an application in the computing device 102. As described above, the color transformation module 108 transforms colors of a visual object, making the colors more perceptible by a colorblind user. Content storage 212 provides local storage of images and video for use with the color transformation module 108.

The communication connection 206 may include, without limitation, a wide area network (WAN) interface, a local area network interface (e.g., WiFi), a personal area network (e.g., Bluetooth) interface, and/or any other suitable communication interfaces to allow the computing device 102 to communicate over the network(s) 104.

The computing device 102, as described above, may be implemented in various types of systems or networks. For example, the computing device may be implemented as a stand-alone system, or may be a part of, without limitation, a client-server system, a peer-to-peer computer network, a distributed network, a local area network, a wide area network, a virtual private network, a storage area network, and the like.

Figure 3:
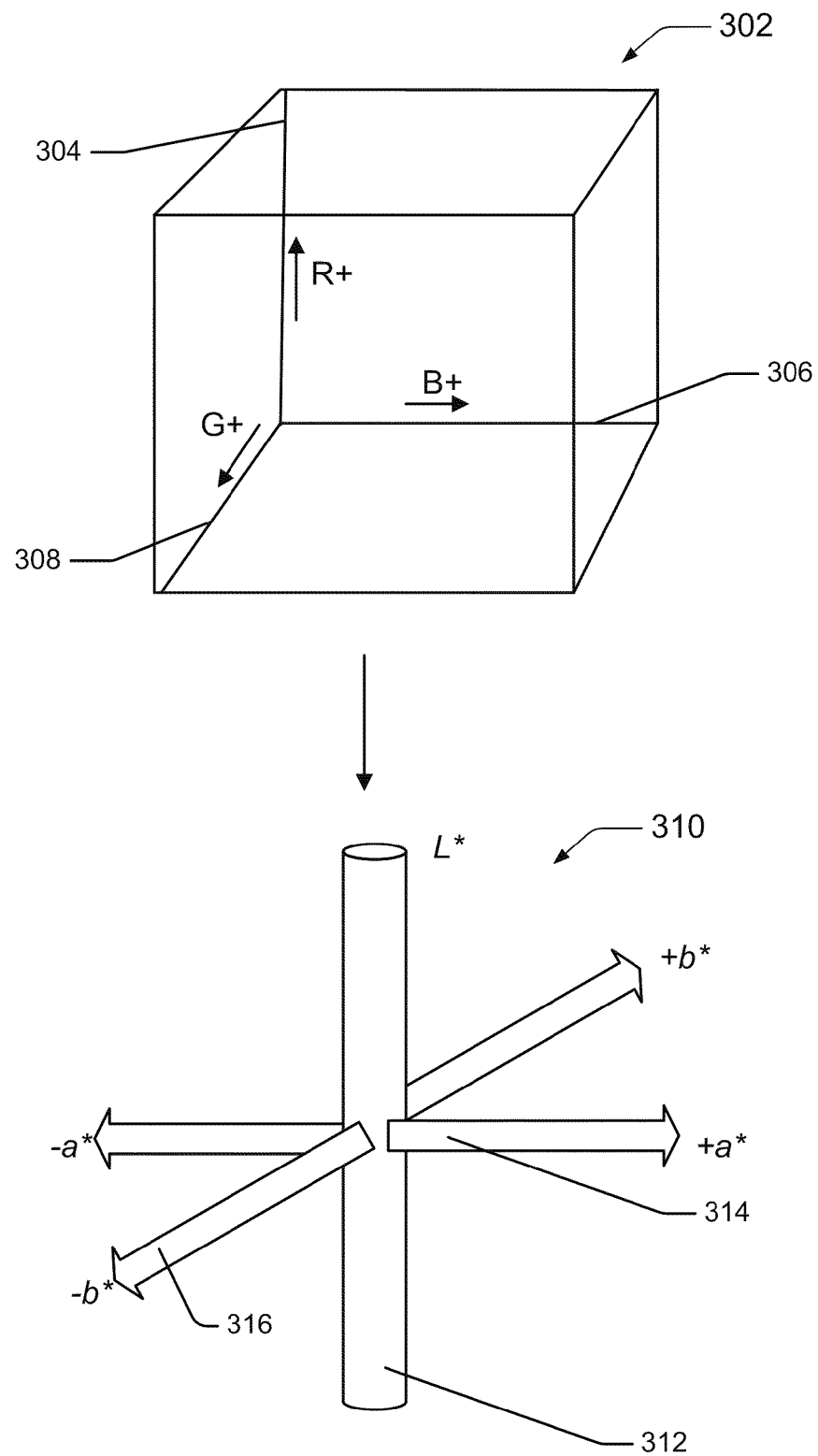
FIG. 3 is a diagram of an exemplary color space transformation within the recoloring framework of FIG. 1.

FIG. 3 illustrates an exemplary color space transformation. Example color space transformation module 214 transforms a color within a red, green, blue (RGB) color space 302 or a cyan, magenta, yellow, and black (CMYK) color space into a color within a CIE L*a*b* (CIELAB) color domain or space 304. The RGB color space model and the CMYK color space model are both designed to render images on devices having limited color capabilities. In contrast, the CIELAB space is designed to better approximate human vision, and therefore provides more subtle distinctions across a larger number of colors.

Each color within the CIELAB color space 304 is represented by a set of coordinates expressed in terms of an L* axis 312, an a* axis 314, and a b* axis 316. The L* axis 312 represents the luminance of the color. For example, if L*=0 the result is the color black and if L*=100 the result is the color white. The a* axis represents a scale between the color red and the color green, where a negative a* value indicates the color green and a positive a* value indicates the color red. The b* axis represents a scale between the color yellow and the color blue, where a negative b* value indicates the color blue and a positive b* value indicates the color yellow.

The L* coordinate 312 closely matches human perception of lightness, thus enabling the L* coordinate to be used to make accurate color balance corrections by modifying output curves in the a* and the b* coordinates, or to adjust the lightness contrast using the L* coordinate. Furthermore, uniform changes of coordinates in the L*a*b* color space generally correspond to uniform changes in a users 106 perceived color, so the relative perceptual differences between any two colors in the L*a*b* color space may be approximately measured by treating each color as a point in a three dimensional space and calculating the distance between the two points.

In one implementation, the distance between the L*a*b* coordinates of one color and the L*a*b* coordinates of a second color may be determined by calculating the Euclidean distance between the first color and the second color. However, it is to be appreciated that any suitable calculation may be used to determine the distances between the two colors.

While there are no simple conversions between an RBG value or a CMYK value and L*, a*, b* coordinates, methods and processes for conversions are known in the art. For example, in one implementation, the color transformation module 214 uses a process referred to herein as a forward transformation process. It is to be appreciated however that any suitable transformation method or process may be used. As illustrated in FIG. 3, the forward transformation method may convert RGB coordinates corresponding to a y-coordinate along the y-axis 304, an x-coordinate along the x-axis 306, and a z-coordinate along the z-axis 308, respectively, to an L* coordinate along the L* axis 312, an a* coordinate along the a* axis 314, and a b* coordinate along the b* axis 316. The forward transformation process is described below. The order in which the operations are described is not intended to be construed as a limitation.

$$L^* = 116 f(Y/Y_n) - 16 \qquad \text{Equation (1)}$$

$$a^* = 500[f(X/X_n) - f(Y/Y_n)] \qquad \text{Equation (2)}$$

$$b^* = 200[f(Y/Y_n) - f(Z/Z_n)] \qquad \text{Equation (3)}$$

where $$f(t) = \begin{cases} t^{1/3} & t > (6/29)^3 \\ \frac{1}{3}\left(\frac{29}{6}\right)^2 t + \frac{4}{29} & \text{otherwise} \end{cases} \qquad \text{Equation (4)}$$

The division of the $f(t)$ function into two domains, as shown above in Equation (4) prevents an infinite slope at t=0. In addition, as set forth in Equation (4), $f(t)$ is presumed to be linear below $t=t_0$, and to match the $t^{1/3}$ part of the function at $t_0$ in both value and slope. In other words:

$$t_0^{1/3} = at_o + b \text{ (match in value)} \qquad \text{Equation (5)}$$

$$\tfrac{1}{3} t_0^{2/3} = a \text{ (match in slope)} \qquad \text{Equation (6)}$$

Setting the value of b to be 16/116 and $\delta$=6/29, Equations (5) and (6) may be solved for a and $t_o$:

$$a = \tfrac{1}{3}\delta^2) = 7.7878037 \qquad \text{Equation (7)}$$

$$t_o = \delta^3 = 0.008856 \qquad \text{Equation (8)}$$

Color transformation module 214 may also perform a reverse transformation process, transforming values from the CIELAB space 304 to the corresponding RGB values or the CMYK values. In one implementation, the reverse transformation process may include the following steps:

1. Define $f_y^{def}=(L^*+16)/116$  Equation (9)

2. Define $f_x^{def}=f_y+a^*/500$  Equation (10)

3. Define $f_z^{def}=f_y-b^*/200$  Equation (11)

4. if $f_y>\delta$ then $Y=Y_n f_y^3$ else $Y=(f_y-16/116)3\delta^2 Y_n$  Equation (12)

5. if $f_x>\delta$ then $X=X_n f_x^3$ else $X=(f_x-16/116)3\delta^2 X_n$  Equation (13)

6. if $f_z>\delta$ then $Z=Z_n f_z^3$ else $Z=(f_z-16/116)3\delta^2 Z_n$  Equation (14)

However, the order in which the process is described is not intended to be construed as a limitation. It is to be appreciated that the reverse transformation process may proceed in any suitable order.

Two types of colorblind conditions are protanopia and deuteranopia. Protanopes and Deuteranopes have a difficult time distinguishing between the color red and the color green. Therefore, a colorblind user affected by one of these conditions may have difficulty with color information represented by the a* value that lies on the a* axis 314.

Figure 4:
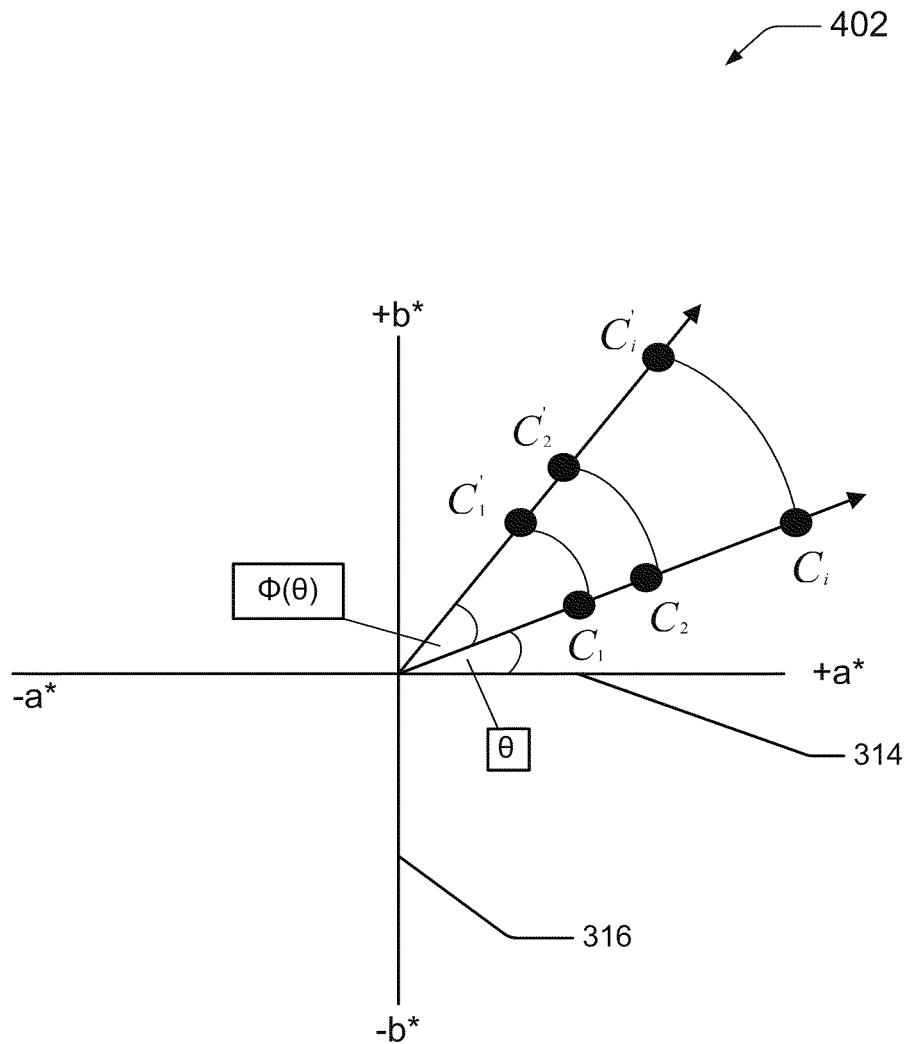
FIG. 4 is a diagram of an exemplary local color rotation within the recoloring framework of FIG. 1.

FIG. 4 illustrates an exemplary local color rotation operation 402 performed by the local color rotation module 216. The local color rotation operation 402 maps an a* value located on the a*-b* plane onto the b* axis 316, enabling the retention of color information represented by the a* value. For example, FIG. 4 illustrates mapping the a* value located on the a*-b* plane onto the b* axis. As illustrated in FIG. 4, $C_1, C_2, \ldots, C_i$ represent color values having the same included angle θ with respect to the a* axis. Because $C_1$, $C_2, \ldots, C_i$ all have the same included angle θ with respect to the a* axis, they all share the same hue. The local color rotation operation 402 maps colors $C_1, C_2, \ldots, C_i$ to new colors $C_1', C_2', \ldots, C_i'$ which lie on another line having the include angle θ+Φ(θ). The described color rotation process simultaneously changes the hue shared by colors $C_1$, $C_2, \ldots, C_i$ such that colors $C_1', C_2', C_i'$ Will still share a hue after the local color rotation operation 402, but the shared hue will be different than the hue shared by colors $C_1, C_2, \ldots, C_i$. In addition, the local color rotation operation 402 preserves the saturation and luminance of the original colors $C_1$, $C_2, \ldots, C_i$.

In one implementation, the local color rotation operation illustrated in FIG. 4 may be formulated as a matrix multiplication. For example, the matrix multiplication may be similar to Equation (15), set forth below:

$$\begin{bmatrix} L' \\ a' \\ b' \end{bmatrix} = \begin{bmatrix} 1 & 0 & 0 \\ 0 & \cos(\phi(\theta)) & -\sin(\phi(\theta)) \\ 0 & \sin(\phi(\theta)) & \cos(\phi(\theta)) \end{bmatrix} \begin{bmatrix} L \\ a \\ b \end{bmatrix} \quad \text{Equation (15)}$$

Where (L', a', b') and (L, a, b) are the CIELAB values of the recolored object, for example transformed visual object 112, and the original visual object 110, respectively. In one implementation, $\phi(\theta)$ is a monotonically decreasing function of θ. Therefore, because the color difference along the b* axis can be distinguished by a good portion of colorblind users, $\phi(\theta)$ decreases to zero when θ approaches $\pm\pi/2$. Accordingly, $\phi(\theta)$ may be defined as:

$$\phi(\theta) = \begin{cases} \phi_{max}\left(1 - \frac{|\theta|}{\pi/2}\right) & \text{if } -\pi/2 \leq \theta < \pi/2 \\ \phi_{max}\left(1 - \frac{|\theta - \pi|}{\pi/2}\right) & \text{if } \pi/2 \leq \theta < 3\pi/2 \end{cases} \quad \text{Equation (16)}$$

In one implementation, a parameter $\phi_{max}$ may be selected by performing a grid search from a pre-defined candidate set, where the pre-defined candidate set maximizes the diversity of colors on the b* axis. Therefore, the pre-defined candidate set may be defined by:

$$\phi\text{max} = \text{argmin}_{\phi_{max} \in S} \sum_{i,j} (b_i' - b_j')^2 \quad \text{Equation (17)}$$

The candidate set may be pre-defined by the user 106, the color transformation module 108, or a combination thereof. In one implementation the candidate set S may be set to $\{-\pi/2, -\pi/3, -\pi/6, 0, \pi/6, \pi/3, \pi/2\}$ however, in other implementations the candidate set may be any suitable set.

Figure 5:
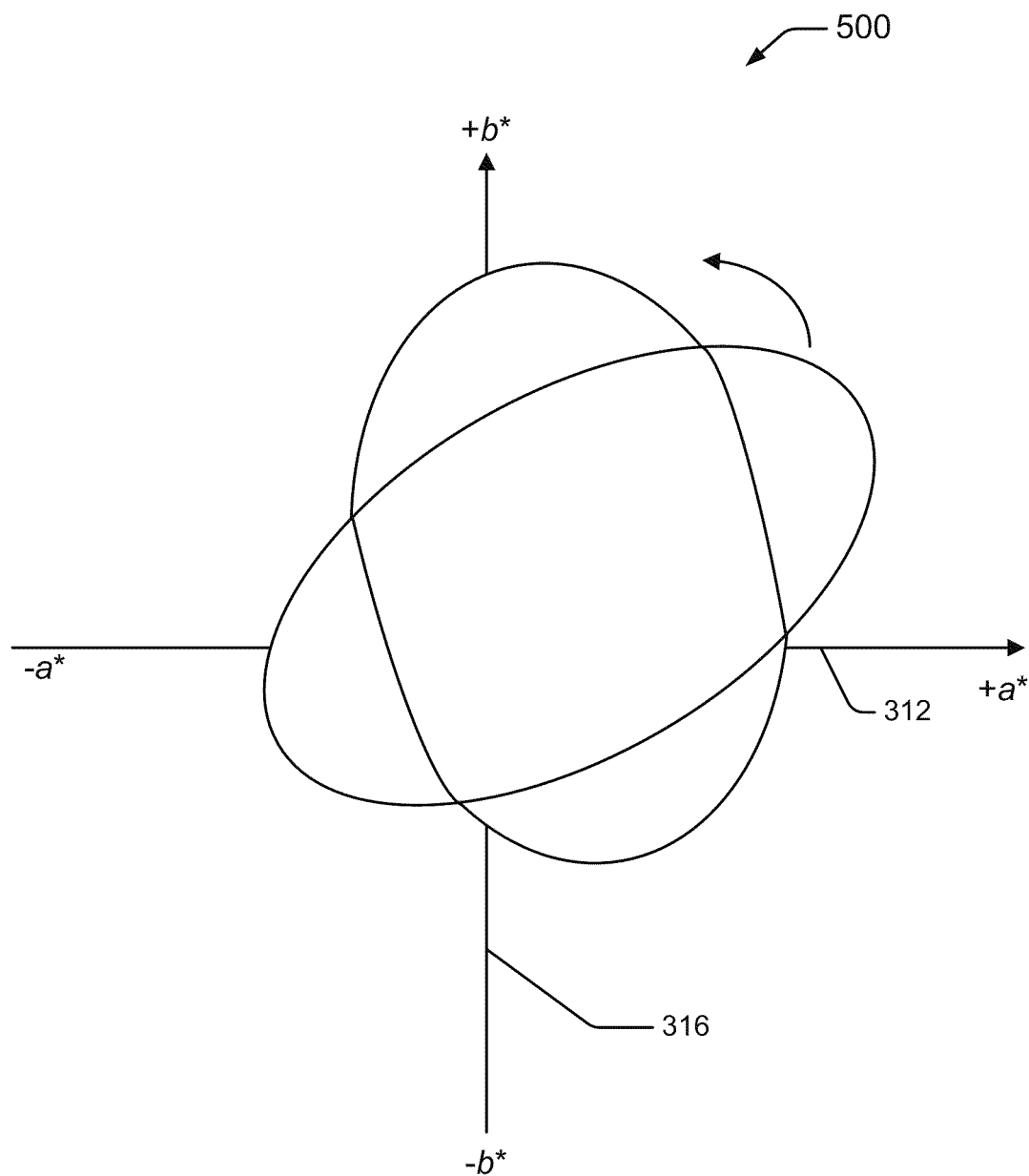
FIG. 5 is a diagram of an exemplary global color rotation within the recoloring framework of FIG. 1.

As illustrated in FIG. 5, the global rotation module 218 performs a second color rotation 500 to refine the results obtained with the local color rotation operation described above.

In one implementation, within the global color rotation operation 500, each color value in the visual object 110 is thought of as a sample within the a*-b* plane of the CIELAB color space. An operation is performed to extract a major color component from within the visual object 110. For example, a 2-dimensional Principle Component Analysis (PCA) may be used to extract the major component. However, it is to be appreciated that any suitable operation may be used. Utilizing the major color component, global rotation module 218 rotates the set of colors at the same angle. Rotating the set of colors at the same angle enables the major color component to remain consistent with the orientation distinguishable by a colorblind user. In one implementation, the distinguishable orientation represents the orientation of a 1-dimensional surface on which the color values $C_1, C_2, \ldots, C_i$ may be distinguished and the rotation angle, $\theta_r$, may be defined as:

$$\theta r = \begin{cases} \theta_d - \theta_m - \pi & \text{if } \theta_d - \theta_m > \pi \\ \theta_d - \theta_m + \pi & \text{if } \theta_d - \theta_m < -\pi \\ \theta_d - \theta_m & \text{otherwise} \end{cases} \quad \text{Equation (18)}$$

where $\theta_d$ and $\theta_m$ are the angles of the distinguishable orientation and the major color component with respect to the a* axis.

Therefore, the global rotation may defined as:

$$\begin{bmatrix} T(L) \\ T(a) \\ T(b) \end{bmatrix} = \begin{bmatrix} 1 & 0 & 0 \\ 0 & \cos\theta_r & -\sin\theta_r \\ 0 & \sin\theta_r & \cos\theta_r \end{bmatrix} \begin{bmatrix} L' \\ a' - \overline{a'} \\ b' - \overline{b'} \end{bmatrix} + \begin{bmatrix} 0 \\ \overline{a'} \\ \overline{b'} \end{bmatrix} \quad \text{Equation (19)}$$

where $\overline{a'}$ and $\overline{b'}$ are the mean values of the a' and b' coordinates, respectively.

The local color rotation operation along with the global color rotation operation maximizes distinction between colors on the a*-b* plane of the CIE LAB color space thus, enhancing the colorblind user's experience.

A colorblind user may also have difficulty distinguishing images while viewing a video stream, causing the user's viewing experience to be diminished. The recoloring process described above is efficient enough to be utilized in the recoloring of images within a video frame. Applying the process described herein enables a color consistency across multiple images within the video, decreasing the likelihood that the colorblind user 106 will become confused by the presentation of a varying image throughout the video.

Figure 6:
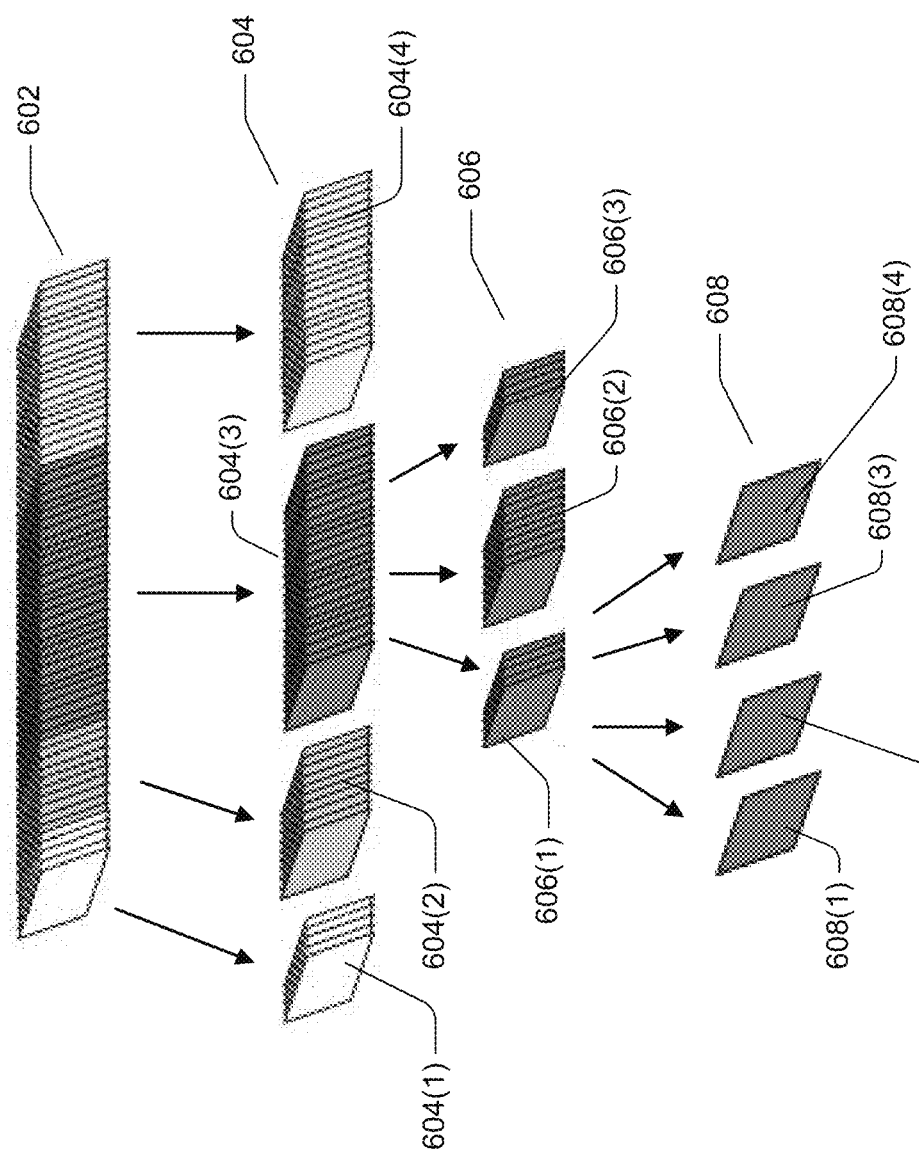
FIG. 6 is an exemplary hierarchical decomposition of video content within the recoloring framework of FIG. 1.

As illustrated in FIG. 6, a video 602 may be broken into one or more scenes 604. Each scene 604 may be broken into one or more shots 606. For example, scene 604(3) is shown broken into shots 606(1), 606(2), and 606(3). Each shot 606 may be broken into one or more frames 608. For example, shot 606(1) is shown broken into frames 608(1), 608(2), 608(3), and 608(4). It is well known in the art that the video 602 is a structured medium, including a temporal correlation between the one or more frames 608 making up each scene. For example, the probability that an image will appear in a shot or a scene will depend primarily on a temporal correlation between the one or more frames 608 within the video data. However, it is to be appreciated that additional factors may also influence the structure of video 602.

The recoloring transformation described above may be computed for a particular frame within a shot, and then applied to the remaining frames within that shot to maintain color consistency between images within the video. More specifically, Equation (16) and Equation (19), as set forth above, are computed for the first frame of a shot, and then the recoloring of the following frames is based on the same settings until the end of that shot. In one implementation, the recoloring process is applied to a video frame rate of 24 fps. However, it is to be appreciated that any suitable video frame rate may be used with the described recoloring process.

The recoloring process described herein also enables the ability to determine recoloring parameters for adjacent shots within video 602. In one implementation, recoloring parameters for adjacent shots may be determined by comparing the first frame of a shot, $frame_1^{k+1}$, with one or more frames of a previous shot, $Shot^k$, to compute a discrepancy value. A discrepancy value may be defined by:

$$D(Shot_k, frame_1^{k+1}) = \frac{\frac{\sum_i diff(frame_1^{k+1}, frame_i^k)}{|Shot^k|}}{\frac{\sum_{i,j} diff(frame_i^k, frame_j^k)}{|Shot^k|^2}} \quad \text{Equation (20)}$$

where, $diff(.,.)$ indicates the difference between two frames, and $|Shot^k|$ denotes the number of frames in $Shot^k$. The difference between two frames, $diff(.,.)$ may be computed by, without limitation, color histogram differences.

Therefore, as set forth above, the numerator of Equation (20) indicates the average difference between the frame $frame_1^{k+1}$ and the frames found in $Shot^k$. If $D(Shot^k, frame_1^{k+1})$ is below a threshold, then there is a high probability that the two shots belong to the same scene. In one implementation, the threshold is set to 2. For example, if $\phi_{max}^k = -\pi/3$, then $\phi_{max}^{k+1}$ can only be selected from the set of values $\{-\pi/2, -\pi/3, -\pi/6, 0\}$. Another max example may be, if $\phi_{max}^k = \pi/6$, then $\phi_{max}^{k+1}$ can only be selected from the set of values $\{0, \pi/6, \pi/3, \pi/2\}$. However, in other implementations the threshold may be set to any suitable value. If the $D(Shot^k,$ $frame_1^{k+1})$ is greater than the set threshold, then the (k+1)-th shot is processed to determine the recoloring parameters independently.

Accordingly, by utilizing identical recoloring parameters for multiple images throughout a shot, and varying recoloring parameters smoothly throughout frames of adjacent shots, the recoloring process remains consistent throughout the one or more frames 608, the one or more shots 606, and the one or more scenes 604 of video 602, providing a more pleasurable experience for the colorblind user 106.

Figure 7:
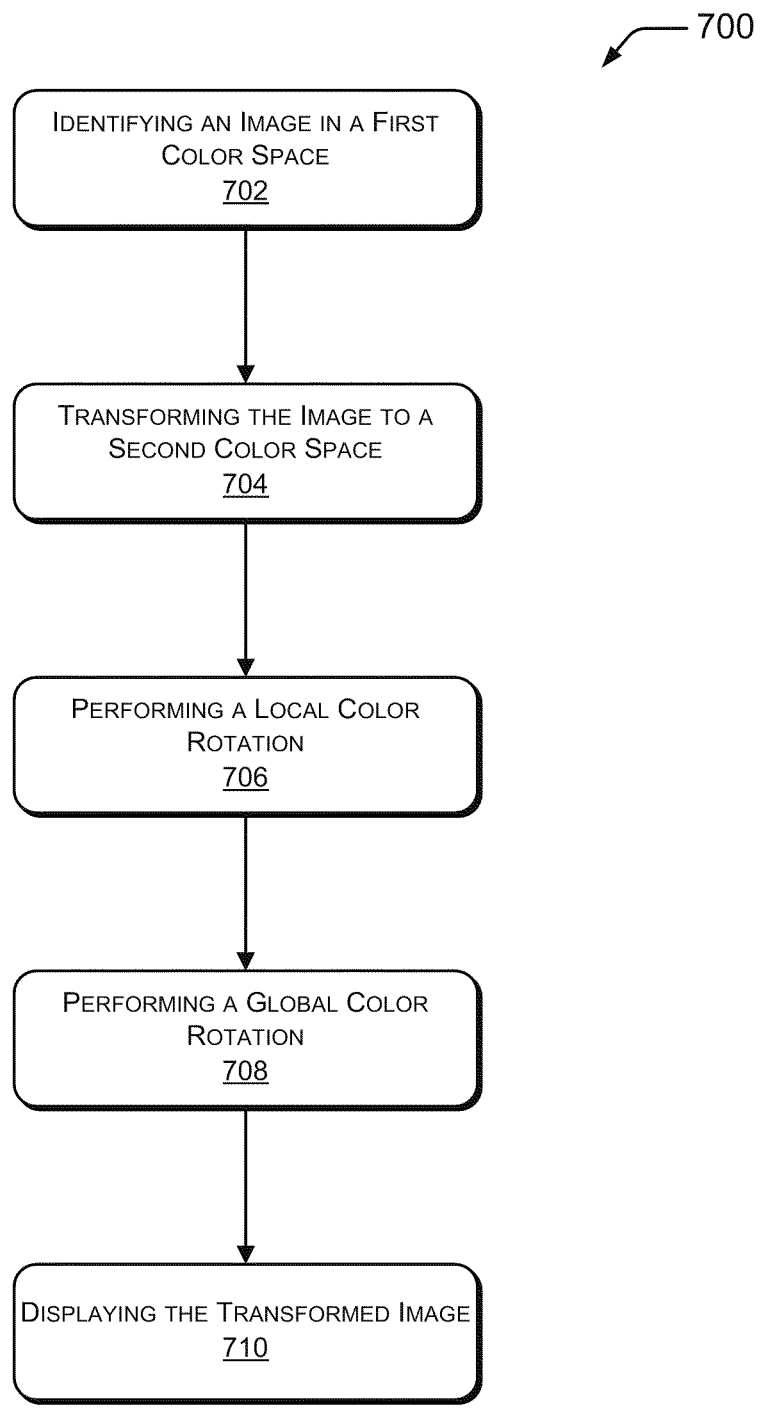
FIG. 7 is a flow chart of an exemplary recoloring process for reworking an image.

FIG. 7 illustrates an exemplary process for recoloring an image as set forth above. At block 702, a visual object 110 is identified, for example, by the colorblind user 106 or the computing device 102. At block 704, color space transformation module 214 transforms the identified image from a first color space to a second color space. For example, the first color space may be an RGB color space or a CMYK color space and the second color space is a CIELAB color space. The transformation may take place, for example, according to a forward transformation.

At block 706, a local color rotation operation is performed on the identified image. For example, local color rotation module 216 rotates colors within the image at a corresponding angle such that the color points within the identified image are rotated away from the a* axis and towards the b* axis within the CIELAB color space.

At block 708, a global color rotation operation is performed. For example, global color rotation module 218 rotates all of the color points within the identified image at the same angle simultaneously, such that the relative orientations of the color points within the image are maintained.

At block 710, the transformed image is displayed. According to the performed color transformation, the transformed image has the same luminance and saturation as the originally identified image. The transformed image enables a colorblind user to distinguish colors that they may not have been able to distinguish in the originally identified image, thus, providing for a more pleasurable viewing experience.

Figure 8:
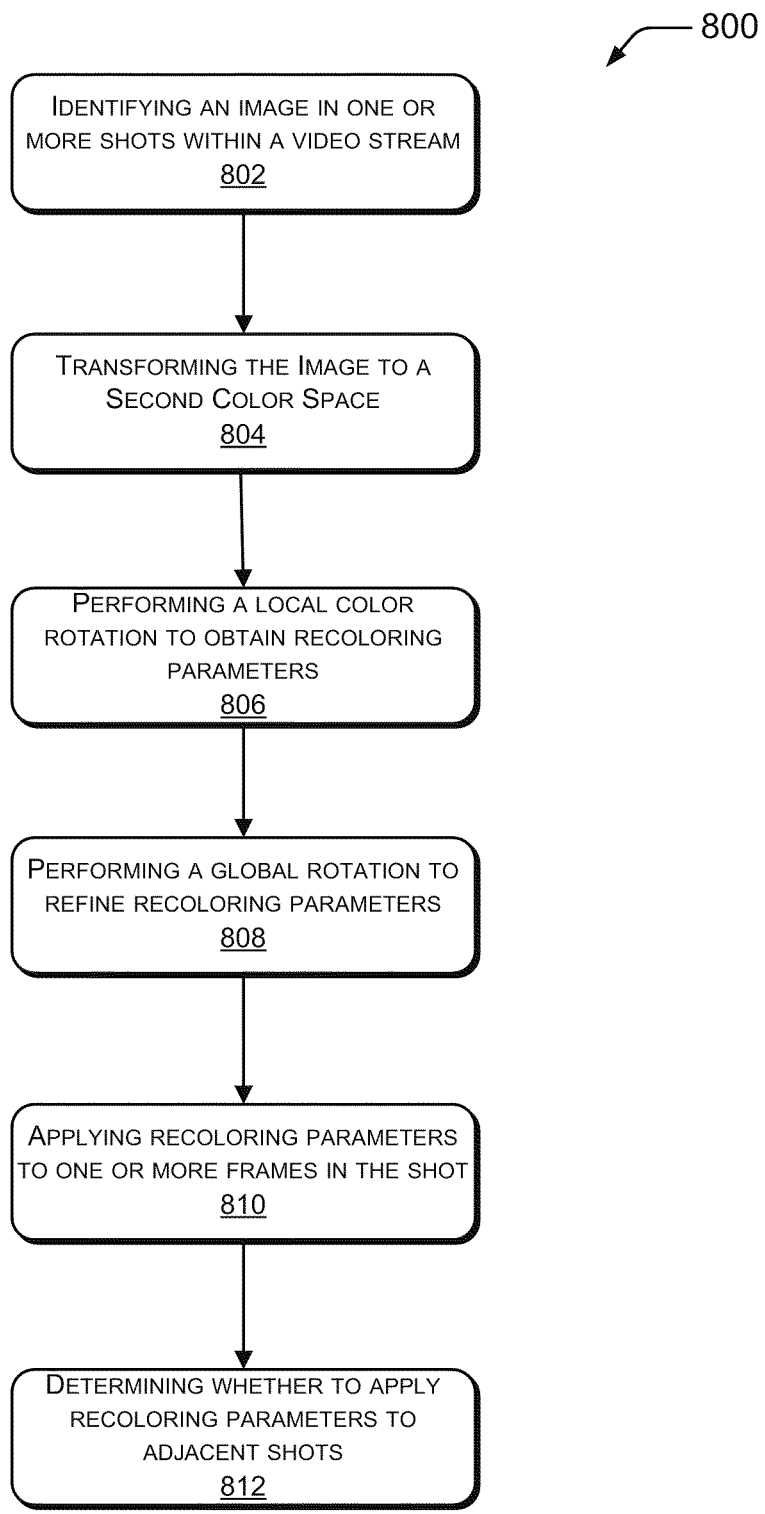
FIG. 8 is a flow chart of an exemplary recoloring process for reworking images in a video.

FIG. 8 illustrates an exemplary process for recoloring video images, as set forth above. At block 802, an image in one or more shots is identified within a video stream. At block 804, color space transformation module 214 transforms the identified image from a first color space to a second color space. For example, the first color space may be an RGB color space or a CMYK color space and the second color space is a CIELAB color space. The transformation may take place, for example, according to a forward transformation.

At block 806 a local color rotation operation is performed on the identified frame. The local color rotation rotates colors within the frame at a corresponding angle such that the color points within the frame are rotated towards the b* axis within the CIELAB color space. This is similar the local color rotation described above with respect to FIG. 7, block 706.

At block 808, a global color rotation operation is performed. The global color rotation rotates all of the color points within the frame at the same angle simultaneously, such that the orientation of the color points within the frame are maintained.

At block 810, the recoloring parameters applied to the frame described above, are applied to the remaining frames within the shot. At block 812, it is determined whether to apply the recoloring parameters to adjacent shots. Such a determination may be based upon a difference between the average difference between the frame $frame_1^{k+1}$ and the frames found in $Shot^k$. If $D(Shot^k, frame_1^{+1})$ is below a threshold, then the two shots have a high probability that the two shots belong to the same scene.

Conclusion

Although a recoloring process for modifying the colors of images and videos to make them more perceptible by color-blind users has been described in language specific to structural features and/or methods, it is to be understood that the subject of the appended claims are not necessarily limited to the specific features or methods described. Rather, the specific features and methods are disclosed as exemplary implementations.

What is claimed is:

1. A computer-implemented method comprising:
implementing a processor to execute computer executable instructions stored on a computer-readable medium to perform operations comprising:
identifying one or more shots within a video stream;
performing a first color rotation and a second color rotation on a first frame of a shot to obtain recoloring parameters;
applying the recoloring parameters to one or more frames remaining in the shot;
determining recoloring parameters for an adjacent shot by comparing the first frame of the shot with one or more frames of the adjacent shot to compute a discrepancy value;
if the discrepancy value is within a given threshold, applying the recoloring parameters determined for the first frame of the shot as the recoloring parameters for the adjacent shot; and
if the discrepancy value is greater than the given threshold, determining the recoloring parameters for the adjacent frame independent of the first frame of the shot.

2. The computer-implemented method of claim 1, wherein the first frame comprises one or more color values in an RGB (red, green and blue) color space or a CMYK (cyan, magenta, yellow and black) color space.

3. The computer-implemented method of claim 2 further comprising transforming the one or more color values from the RGB color space or the CMYK color space to a CIELAB (CIE L*a*b*) color space.

4. The computer-implemented method of claim 1, wherein the first color rotation comprises a local color rotation operation utilizing an angle corresponding to a color value within a set of one or more color values.

5. The computer-implemented method of claim 1, wherein the second color rotation comprises a global color rotation operation rotating a set of one or more color values at a same angle such that relative orientations of color points within the first frame are maintained.

6. The computer-implemented method of claim 1, further comprising selecting a recoloring parameter of the recoloring parameters determined for the first frame of the shot by performing a grid search from a pre-defined candidate set, where the pre-defined candidate set maximizes diversity of one or more colors within the first frame.

7. The computer-implemented method of claim 6, wherein the pre-defined candidate set is $\{-\pi/2, -\pi/3, -\pi/6, 0, \pi/6, \pi/3, \pi/2\}$.

8. The computer-implemented method of claim 6, wherein the pre-defined candidate set is user-defined.

9. A system comprising:
one or more processors;
memory;
a color transformation module stored in the memory and executable by the one or more processors that is configured to:
identify one or more shots within a video stream;
perform a first color rotation and a second color rotation on a first frame of a shot of the one or more shots to obtain recoloring parameters;
apply the recoloring parameters to one or more frames remaining in the shot;
determine recoloring parameters for an adjacent shot by comparing the first frame of the shot with one or more frames of the adjacent shot to compute a discrepancy value;
apply the recoloring parameters determined for the first frame of the shot as the recoloring parameters for the adjacent shot if the discrepancy value is within a given threshold; and
determine the recoloring parameters for the adjacent shot independent of the first frame of the shot if the discrepancy value is greater than the given threshold.

10. The system of claim 9, wherein the first frame comprises one or more color values in an RGB (red, green and blue) color space or a CMYK (cyan, magenta, yellow and black) color space.

11. The system of claim 10, wherein the color transformation module is further configured to transform the one or more color values from the RGB color space or the CMYK color space to a CIELAB (CIE L*a*b*) color space.

12. The system of claim 9, wherein the first color rotation comprises a local color rotation operation utilizing an angle corresponding to a color value within a set of one or more color values.

13. The system of claim 9, wherein the second color rotation comprises a global color rotation operation rotating a set of one or more color values at a same angle such that relative orientations of color points within the first frame are maintained.

14. The system of claim 9, wherein the color transformation module is further configured to select a recoloring parameter by performing a grid search from a pre-defined candidate set, wherein the pre-defined candidate set maximizes diversity of one or more colors within the first frame.

15. The system of claim 14, wherein the pre-defined candidate set comprises $\{-\pi/2, -\pi/3, -\pi/6, 0, \pi/6, \pi/3, \pi/2\}$ or a user-defined set.

16. A method comprising:
under control of one or more processors configured with executable instructions,
identifying one or more shots within a video stream;
performing a first color rotation and a second color rotation on a first frame of a shot to obtain recoloring parameters, wherein the first color rotation comprises a local color rotation operation utilizing an angle corresponding to a color value within a set of one or more color values, and the second color rotation comprises a global color rotation operation rotating the set of one or more color values at a same angle such that relative orientations of color points within the first frame are maintained;
applying the recoloring parameters to one or more frames remaining in the shot;
determining recoloring parameters for an adjacent shot by comparing the first frame of the shot with one or more frames of the adjacent shot to compute a discrepancy value;
if the discrepancy value is within a given threshold, applying the recoloring parameters determined for the first frame of the shot as the recoloring parameters for the adjacent shot; and if the discrepancy value is greater than the given threshold, determining the recoloring parameters for the adjacent frame independent of the first frame of the shot.

\* \* \* \* \*